(12) United States Patent
Murata et al.

(10) Patent No.: US 6,486,132 B2
(45) Date of Patent: Nov. 26, 2002

(54) IMMUNOMODULATOR, IMMUNOMODULATOR FOOD AND IMMUNOMODULATOR FEED

(75) Inventors: Kousaku Murata, Kyoto (JP); Yasuki Fukuda, Gifu (JP); Mizuo Yajima, Tokyo (JP); Hiroichi Katsuyama, Tokyo (JP)

(73) Assignee: Asama Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/324,490

(22) Filed: Jun. 2, 1999

(65) Prior Publication Data

US 2001/0051609 A1 Dec. 13, 2001

(30) Foreign Application Priority Data

Mar. 19, 1999 (JP) .............................. 11-075396

(51) Int. Cl.$^7$ ...................... A01N 43/04; C07H 21/02; A61K 39/108; A61K 39/05; A61K 39/07
(52) U.S. Cl. ..................... 514/44; 536/23.1; 424/234.1; 424/241.1; 424/245.1; 424/246.1
(58) Field of Search ............................ 424/164.1, 93.1, 424/184.1, 241.1, 246.1, 249.1, 248.1, 234.1, 245.1; 435/6, 91.1; 536/23.1; 514/44

(56) References Cited

U.S. PATENT DOCUMENTS

| | | | |
|---|---|---|---|
| 4,346,118 A | 8/1982 | Islam | 426/335 |
| 5,830,877 A | * 11/1998 | Carson et al. | 514/44 |

FOREIGN PATENT DOCUMENTS

| | | |
|---|---|---|
| EP | 0 167 710 | 1/1986 |
| EP | 0 362 471 | 4/1990 |
| EP | 0 730 867 | 9/1996 |
| JP | 900296954 | 6/1992 |
| WO | WO 95/05461 | 2/1995 |

OTHER PUBLICATIONS

Merriam Webster's Collegiate Dictionary, 10th Ed. Springfield, MA, 1997.*
Mors et al. Trends in Microbiol. 6(11): 449–53, Nov. 1998.*
Ethchart et al. J. Gen. Virol. 78(7): 1577–1580, 1997.*
Arnaudova et al. J Rheumatology. 20(8): 1445–1446, Aug. 1993.*
Doerfler et al. Wiener Klinische Wochenschrift. 110(2): 40–44, Jan. 1998.*
Krieg et al. Nature. 374: 546–549, Apr. 1995.*
Kato et al. Microbiology Immuno. 27(7): 611–618, 1983.*
Yamamoto et al. Microbiol. Immuno. 36(9): 983–997, 1992.*
Alberts et al. Molecular Biology of the Cell. 3rd Ed. Garland Publishing, Inc. p. 292–3, 1994.*
Continuous Fermentation of L–glutamic Acid (II), Kinetic Analysis of Growth Phase and its Application to Continuous Fermentation (Part I), Akio Mimura et al, pp. 275–281, Osaka University(1963).
Macrophage Activation by *Lactobacillus casei* in Mice, Ikuo Kato et al, Microbiol. Immunol., vol. 27 (7), pp. 611–618, 1983.
Analysis of CpG suppression in methylated and nonmethylated species, Daniel F. Schorderet et al, Proc. Natl. Acad. Sci., USA, vol. 89, pp. 957–961, Feb. 1992 Genetics.
DNA from Bacteria, but Not from Vertebrates, Induces Interferons, Activates Natural Killer Cells and Inhibits Tumor Growth, Saburo Yamamoto et al, Microbiol. Immunol., vol. 36, (9), pp. 983–997, 1992.
CpG motifs in bacterial DNA trigger direct B–cell activation, Arthur M. Krieg et al, Nature, vol. 374, pp. 546–549, Apr. 1995.
Rapid Immune Activation by CpG Motifs in Bacterial DNA, Ae–Kyung Yi et al, The Journal of Immunology, 1996, vol. 157, pp. 5394–5402.
Novel physiological function of DNA: Suppresion of Proliferation of Eukaryotic Microbiological Cells by Procaryotic DNA, Keiko Matsutani et al, Nippon Nogeikagaku Kaishi 1997 Annual Convention held in Tokyo, 4 pages.
CpG distribution patterns in methylated and non–methylated species, Tom S. Shimizu et al, Gene, vol. 205, 1997, pp. 103–107.
Fungistatic and Fungicidal Compounds for Human Pathogens, Ernest M. Walker, Jr. et al, Disinfectants and Antiseptics: B by Type of Microorganisms, Chapter 24, pp. 385–410, 1991.

* cited by examiner

*Primary Examiner*—Scott D. Priebe
*Assistant Examiner*—Shin-Lin Chen
(74) *Attorney, Agent, or Firm*—Flynn, Thiel, Boutell & Tanis, P.C.

(57) ABSTRACT

To provide an immunomodulator in which DNA can be administered orally or percutaneously, not through injection, or can be taken daily like a food, or an immunomodulator food or feed. DNA derived from cells of procaryotes such as *Bacillus subtilis*, lactic acid bacteria, amino acid producing bacteria and *Escherichia coli* is added to food or molded to be able to administer the same orally, percutaneously or permucosally, or formed into food, feed or the like.

7 Claims, No Drawings

IMMUNOMODULATOR, IMMUNOMODULATOR FOOD AND IMMUNOMODULATOR FEED

BACKGROUND OF THE INVENTION

1. Field of the Invention

The present invention relates to an immunomodulator, an immunomodulator food, an immunomodulator feed, a troche and an agent for external application, having DNA derived from the cells of procaryotes.

2. Related Art

Appropriate activation of an immunological activity of man and animals is considered important to become resistant to infectious diseases including common cold, to primary prevention of cancers, and checking allergic and atopic diseases and the like. It has been known that DNA from the cells of procaryotes has an immunopotentiation activity and DNA from the cells of eucaryotes does not. However, the immunomodulation activity of DNA is inactivated through deoxyribonuclease treatment in vitro (S. Yamamoto et al., Microbiol. Immunol., Vol. 36(9), 983–997, 1992). It has been so far considered that since a digestive juice enzyme of humans and animals contains deoxyribonuclease, the immunomodulation activity of DNA is effective only through administration thereof by injection.

Since the administration by injection damages the body, however, it is inappropriate for repeated administration. In order to improve the physical condition for which immunopotentiation is deemed necessary, it is actually rather important that the purpose is achieved by daily intake of DNA through food or by contact with the cutaneous mucosa.

SUMMARY OF THE INVENTION

Accordingly, an object of the present invention is to provide an immunomodulator in which DNA can be administered not through injection, but, for example, orally or percutaneously, or can daily be taken in food or feed.

As a result of extensive investigation in order to solve the above-mentioned problem, the present inventors have found that the exhibition of immunomodulation activity is unexpectedly obtained by either oral or percutaneous administration of DNA derived from procaryotes such as Bacillus subtilis and lactic acid bacteria. This finding has led to the completion of the present invention.

That is, the present invention is to provide an immunomodulator, an immunomodulator food or an immunomodulator feed containing DNA derived from cells of procaryotes as an active ingredient.

The invention provides a method of modulating the immunofunction by administering orally, percutaneously or permucosally a pharmacologically effective amount of DNA extracted from cells of a procaryote to human being or animal.

It is preferable that the DNA is a product produced by culturing cells of a procaryote, harvesting the cells, dissolving the cells with a bacterial cell wall digesting enzyme in water and adding ethanol to the lysate solution to isolate a DNA product. The DNA may be the DNA extraction product or the ethanol-insoluble fraction in ethanol or an aqueous ethanol of bacterial cells. The product may be well obtained at about 40% volume/volume aqueous ethanol.

It is preferable that the DNA has at least 8 bases and includes at least one CpG sequence. The DNA a sodium salt of the same.

In the invention, the reticuloendothelial system is activated. Accordingly, an infectious disease can be treated.

In the invention, the growth of a tumor is inhibited.

In the invention, an autoimmune cutaneous disease is treated.

DETAILED DESCRIPTION OF THE INVENTION

In the present invention, the procaryotes are not necessarily specific bacteria. However, in view of the safety, Bacillus subtilis (genus Bacillus), lactic acid bacteria (lactobacilli), amino acid-producing bacteria, Escherichia coli and the like can be mentioned. Of these, Bacillus natto, lactic acid bacteria and amino acid producing bacteria, which are used in production of foods, are especially preferable. As lactic acid bacteria, preferably, Lactobacillis casei, Lactobacillus acidophilus, Lactobacillus del-brueckii, Streptococcus faecalis, Biphidobacterium longum and the like can be mentioned. As amino acid producing bacteria, for example, Corynebacterium glutamicum, Corynebacterium herculis, Brevibacterium flavum, Microbacterium ammoniaphilum and Escherichia coli can be mentioned.

DNA can be removed from cells of procaryotes by a known method. For example, Corynebacterium glutamicum is cultured in an appropriate medium. The cells are then harvested through centrifugation, washed with a 0.85% physiological saline solution, and thereafter suspended in a physiological saline solution or purified water. The cells are dissolved with the addition of a bacterial cell wall digesting enzyme such as a lysozyme. To this solution is gradually added pure ethanol that has been cooled. DNA which is insolubilized at an ethanol concentration of 40% volume/volume is wound up on a glass bar. The resulting DNA is washed with 60% volume/volume ethanol, with 70% volume/volume ethanol and with 80% volume/volume ethanol in this order, and dried in vacuo to obtain a high-purity DNA product.

The resulting DNA product can be added as such to food, feed or beverages. It is also possible that the resulting DNA product is mixed with a filler, an excipient and the like which are ordinarily the production of pharmaceuticals, and the mixture is molded into an appropriate form as required to provide preparations or food. It can further be formulated into a solution.

The immunomodulation activity of the procaryotic DNA is chemically stable. Even when it was added to an ordinary feed, it neither reacted with feed ingredients nor deactivated with heat as described in Examples 4 and 5. This shows that during the step of producing the immunomodulator food and the immunomodulator containing this DNA, cooking or heat sterilization treatment can freely be practiced. The immunomodulation activity of the DNA derived from procaryotes is, as mentioned above, stable, and no aging deterioration is observed. Accordingly, the activity is not lost during the storage or the distribution of this product.

In case of administering DNA as an immunomodulator in the form of an aqueous solution, it is especially rendered to have a low-molecular weight through ultrasonic treatment (sonication) or restriction endonuclease treatment, whereby the viscosity decreases and it becomes convenient for drinking. In the sonication, for example, purified water is added to the DNA product such that the concentration reaches 1%, and an ultrasonic wave is applied thereto for from 5 minutes to 20 minutes while cooling the same with ice water. It has been known that the DNA molecule derived from procaryotic cells exhibits immunomodulation activity because the base sequence is characteristic and procaryotic cells, unlike eucaryotic cells, contain a large number of CpG sequences (A. M. Krieg et al., Nature, Vol. 374; pp. 546–549, 1995). Accordingly, in the restriction endonuclease treatment, the restriction endonuclease is not particularly selected so long as it does not cleave a CpG linkage. The restriction endonuclease treatment may be conducted by an ordinary endonuclease treatment method.

The food is not particularly limited when DNA is provided in food through addition. DNA can be added to, for example, staple foods such as bread, noodles and rice; side dishes such as boiled fish paste (kamaboko), ham, sausage, cooked salad and pickled vegetables; seasonings such as soy-bean paste (miso), soy sauce, soup, sauce and dressing; dairy products such as milk, cocoa drinks, butter, margarine, cheese and ice cream; confectioneries such as cookies, biscuits, wafers, candies and chewing gum; processed fruit products such as fruit juice drinks and jam; and pet feed, fishery and stockbreeding feeds and the like.

When DNA in the present invention is applied as a main agent, it can orally be used in powder, granules, dispersions, capsules, sweets, drinks or the like. In addition, it can be used percutaneously as an ointment, a compress, a solution or a bath product and permucosally as a troche, a suppository or a gargle. In the percutaneous use, the above-mentioned low-molecular product is preferable. When the immunomodulator of the present invention is used through oral administration, the standard intake is between 0.001 and 100 g/day equivalent to DNA, and there is no specials upper limit. The concentration of DNA in the percutaneous application is between 0.001 and 100%, but it is not particularly limited.

In accordance with the present invention, it is possible to provide an immunomodulator in which DNA can be administered orally or percutaneously, not through injection, or can daily be taken in food or feed, and further to provide an immunomodulator food or feed.

EXAMPLES

The present invention is illustrated more specifically by giving the following Examples. By the way, in the Examples, % and parts are both on the weight basis.

Example 1

Extraction of Cellular DNA

Corynebacterium glutamicum IAM 12435 was inoculated into an L-shaped tube containing 10 ml of nutrient broth, and incubated while being shaken at 30° C. for 7 hours. One milliliter of this culture solution was inoculated in each of 10 conical flasks (Erlenmeyer flask) having a capacity of 500 ml and containing 100 ml of a medium of Mimura et al. (Hakko Kogaku Zasshi, vol. 41, No. 5, pp. 275–281, 1963), and incubated while being shaken at 30° C. for 21 hours. This culture was further added to 24 liters of the medium of Mimura et al., and the incubation was continued in a jar fermenter. Then, penicillin G was added at a concentration of 0.2 units/ml in the logarithmic phase. The cells were harvested through centrifugation to obtain approximately 1,000 g of wet cells. The wet cells were washed by centrifugation once with a physiological saline solution. Then, 5 liters of a physiological saline solution were added to the cells for suspension. One gram of egg-white lysozyme was added thereto while being stirred. After the stirring at 37° C. for 2 hours, the temperature was elevated to 65° C. to destroy the cells. Pure ethanol, which had been cooled to −20° C., was gradually added thereto. DNA insolubilized at the ethanol concentration of 40% was wound up with a glass rod. The resulting DNA was rinsed with 60% ethanol, with 70% ethanol and with 80% ethanol in this order, and then dried in vacuo to obtain 5 g of a DNA product.

Example 2

Sonication of DNA

The DNA product obtained in Example 1 was dissolved in purified water at a concentration of 10 mg/ml. Seventy milliliters of the DNA solution were charged into a container of a sonicator (manufactured by Kubota Seisakusho K.K., Insonator Model 201M), and sonicated at 90 kHz for 5 minutes while being cooled at 0° C. To this was added 2 volumes of pure cold ethanol of −20° C. The mixture was allowed to stand at −20° C. for 24 hours. The precipitate was then centrifuged, and dried in vacuo to obtain 700 mg of a sonicated DNA product.

Example 3

Restriction Endonuclease Decomposition of DNA

Purified water was added to the DNA product obtained in Example 1 to dissolve the same at a concentration of 10 mg/ml as DNA. To 1 ml of this mixture was added 1 ml of a 100 mM tris hydrochloride buffer solution of pH 7.5 containing 10 mM $MgCl_2$, 1 mM Dithiothreitol and 100 mM NaCl. Further, 10,000 units of restriction endonuclease EcoRI (made by Takara Shuzo Co., Ltd.) were added thereto, and the reaction was conducted at 37° C. for 2 hours. To this was added 0.2 ml of a 3M sodium acetate solution, and 2.5 volumes of cold pure ethanol of −20° C. was added thereto. The mixture was allowed to stand at −20° C. for 24 hours, and the precipitate was then centrifuged. The precipitate was rinsed with 60% ethanol, with 70% ethanol and with 80% ethanol in this order, and dried in vacuo to obtain 8 mg of the restriction endonuclease-treated DNA product.

Example 4

Activation of a Reticuloendothelial System with Feed or Drinking Water Containing Bacterial DNA As an index of an immunomodulation activity, the influence of bacterial DNA on activation of a reticuloendothelial system was examined. Since administration with drinking water required a decreased viscosity of a solution, a sonicated product was used. One group consisted of 5 ICR-strain female mice which were 6 weeks old, and a DNA-containing feed or DNA-containing drinking water containing 0.1% or 1%, as DNA, of the product was administered thereto. After the administration was continued for 7 days, colloidal carbon (Pelican Ink) was intravenously administered in an amount of 8 mg/100 g weight. After 0, 3, 6, 9, 12 and 15 minutes, 20 μl of the blood were obtained by retroorbital puncture, and added to 4 ml of 0.1% sodium carbonate. An absorbance at a wavelength of 675 nm was measured. The half life (clearance rate t ½) of carbon from the blood was calculated by the method of Kato et al. (I. Kato et al., Microbiol. Immunol., Vol. 27(7), 611–618, 1983). The results are shown in Table 1.

TABLE 1

| Treatment group | Number of animals | t 1/2 ± SD min | P |
|---|---|---|---|
| Administration of 0.1% C. glutamicum IAM 12435 DNA-containing feed | 5 | 9.0 ± 1.6 | <0.05 |
| Administration of 1% C. glutamicum IAM 12435 DNA-containing feed | 5 | 4.9 ± 2.0 | <0.01 |
| Administration of 0.1% sonicated C. glutamicum IAM 12435 DNA-containing drinking water | 5 | 8.1 ± 2.3 | <0.05 |
| Administration of 1% sonicated C. glutamicum IAM 12435 DNA-containing drinking water | 5 | 4.1 ± 1.5 | <0.01 |
| Administration of 1% B. natto DNA-containing feed | 5 | 6.6 ± 0.9 | <0.01 |
| Administration of 1% sonicated B. natto DNA-containing drinking water | 5 | 5.6 ± 1.1 | <0.01 |
| Administration of 1% yeast DNA-containing feed | 5 | 12.0 ± 0.7 | ns |
| Administration of 1% sonicated yeast DNA-containing drinking water | 5 | 11.9 ± 2.2 | ns |
| Untreated group | 5 | 13.5 ± 1.8 | |

As is clear from the results in Table 1, the activation of the reticuloendothelial system was observed in the DNA derived from the bacterium, whereas the activation was not observed in the DNA from the eucaryotic cell (yeast).

*B. natto* DNA was produced as in Example 1. With respect to yeast DNA, *Saccharomyces cerevisiae* FT-1 was inoculated in a YPD medium (2.0% glucose, 1% yeast extract, 2.0% bacto-peptone, pH 5.0), and incubated at 30° C. The cells were subjected to bacteriolysis through treatment with 10 units/ml of Zymolase (made by Seikagaku Kogyo K.K.) in a Trishydrochloride buffer solution of pH 7.0 containing 0. 1 mM EDTA. Then, SDS was added thereto at a rate of 2% to destroy the yeast nucleus. Further, the product was treated with cold pure ethanol as in Example 1 to form a yeast DNA product.

Further, sonicated products of *B. natto* DNA and yeast DNA were produced as in Example 2.

Example 5

Inhibition of Tumor Growth by a Feed or Drinking Water Containing Bacterial DNA

As a bacterial DNA sample, DNA derived from *C. glutamicum* IAM 12435 (Example 1) was used, and as a comparison and control, DNA derived from yeast as described in Example 4 was used. Female BALB/c mice were given feed and water ad libitum. The feed contained 1%, as DNA, of each of the DNA products (heat-treated at a product temperature of 90° C. for 20 minutes) and the drinking water contained 1%, as DNA, of each of the DNA products (heat-treated at 90° C. for 20 minutes). Two weeks later, the Meth-A tumor was implanted subcutaneously of the back portion at 1×10$^6$ cells. Further, the DNA-containing feed was continuously given. On the 15th day after the tumor implantation, the tumor was extracted, and the weight thereof was measured. The results are shown in Table 2.

TABLE 2

| Treatment group | Number of animals | Tumor weight mg ± SE | P |
|---|---|---|---|
| Administration of bacterial DNA-containing feed | 19 | 463 ± 61 | <0.05 |
| Administration of sonicated bacterial DNA-containing drinking water | 20 | 349 ± 52 | <0.05 |
| Administration of yeast DNA-containing feed | 10 | 650 ± 323 | ns |
| Administration of sonicated yeast DNA-containing feed | 10 | 882 ± 223 | ns |
| Untreated group | 18 | 769 ± 80 | |

The production of the feed was conducted as follows. That is, a mixed feed was produced in a usual manner according to a recipe of 20 parts of casein, 10 parts of corn oil, 30 parts of mineral mix (made by Oriental Yeast Co., Ltd.), 2.0 parts of vitamin mix (made by Oriental Yeast Co., Ltd.), 49 parts of corn starch, 10 parts of sugar, 5 parts of cellulose and 1.0 part of DNA prepared in Example 1.

As is clear from Table 2, the tumor growth was inhibited by the administration of the DNA derived from cells of the procaryote.

Example 6

Preparation of an Agent for External Application

A preparation for skin application was produced according to the following recipe.

| | |
|---|---|
| sonicated C. glutamicum IAM 12435 DNA | 1.0% |
| glycerin | 5.0% |
| propylene glycol | 4.0% |
| oleyl alcohol | 0.1% |
| ethanol | 5.0% |
| benzoic acid | 0.05% |
| purified water | 84.9% |

Sonicated DNA (Example 2), glycerin and propylene glycol were added to, and dissolved in, purified water. Meanwhile, oleyl alcohol and benzoic acid were dissolved in ethanol at room temperature. This solution was added to the purified water portion, and solubilized. The mixture was heated at 90° C. for 20 minutes, filtered, and then filled.

Example 7

Preparation of an Agent for External Application

A preparation for skin application was produced according to the following recipe.

| | |
|---|---|
| restriction endonuclease-treated C. glutamicum IAM 12435 DNA | 1.0% |
| glycerin | 5.0% |
| propylene glycol | 4.0% |
| oleyl alcohol | 0.1% |
| ethanol | 5.0% |

-continued

| restriction endonuclease-treated C. glutamicum IAM | |
|---|---|
| benzoic acid | 0.05% |
| purified water | 84.9% |

Restriction endonuclease-treated DNA (Example 3), glycerin and propylene glycol were added to, and dissolved in, purified water. Meanwhile, oleyl alcohol and benzoic acid were dissolved in ethanol at room temperature. This solution was added to the purified water portion, and solubilized. The mixture was filtered, and then filled.

Example 8

Preparation of a Troche

A troche was produced according to the following recipe for 100 tablets.

| | |
|---|---|
| white sugar (fine powder) | 100 g |
| gum arabic (fine powder) | 8 g |
| sonicated DNA | 5 g |
| menthol | 0.6 mg |
| thymol | 0.6 mg |
| eucalyptus oil | 0.002 ml |
| lemon oil | 0.002 ml |
| water | suitable amount |

Granules were produced by a wet method, and formed into a troche such that one tablet was approximately 1.2 g.

Example 9

Ninety milligrams of the *C. glutamicum* IAM 12435 DNA powder obtained in Example 1, 30 mg of starch and 180 mg of Avicell (cellulose, made by Asahi Chemical Industry Co., Ltd.) were mixed, and a tablet-type food was produced in a usual manner such that one tablet was 300 mg.

Example 10

Purified water was added to 0.05 part of the *C. glutamicum* IAM 12435 DNA powder obtained in Example 1, and 10 parts of cocoa butter, 7 parts of granulated sugar, 7 parts of milk and 0.05 part of an emulsifying agent were also added to adjust the total amount to 100 parts, and a cocoa drink was produced in a usual manner.

Example 11

Purified water was added to 0.2 part of *C. glutamicum* IAM 12435 obtained in Example 2, 10 parts of cocoa butter, 7 parts of granulated sugar, 7 parts of milk and 0.05 part of an emulsifying agent to adjust the total amount to 100 parts, and a cocoa drink was produced in a usual manner.

Example 12

DNA-containing raw pasta was produced using a roll-type noodle-making machine. The recipe was: 650 g of a semi-strong flour, 350 g of a durum flour (semolina), 10 g of an egg-white powder, 8 g of a york powder, 15 g of gliadin, 30 g of ethanol, 100 mg of DNA (Example 1) and 280 g of water.

Example 13

Five-hundred grams of uncooked rice which had been washed with water and from which water had been drained were cooked by adding thereto 500 g of water and 300 mg of DNA (Example 1).

In a group of 12 persons who ate the cooked rice of this recipe at two meals a day for one winter (3 months), only 2 persons suffered from influenza. Meanwhile, in a DNA-non-addition group (12 persons), 8 persons suffered from influenza. Thus, the immunomodulation activity of DNA was identified.

Example 14

A powdery formula feed was produced by uniformly mixing 39 parts of 65% white fish meal, 5 parts of a soybean cake, 2 parts of a mixture of vitamin $B_1$ and other vitamins and 2 parts of calcium, phosphorus and other minerals with 2 parts of carboxymethyl cellulose and 0.1 part of DNA obtained in Example 1.

Example 15

Generalized scleroderma is known as an autoimmune cutaneous disease, and interferon is deemed to be useful for its therapy. A therapeutic effect of the DNA agent for external application obtained in Example 6 was examined using a scleroderma mouse model treated with bleomycin.

One group consisted of six female BALB/c mice which were 6 weeks old. Bleomycin was administered at a dose of 10 µg/0.1 ml to two groups of mice subcutaneously of the dorsolateral portion every day for 4 weeks. The DNA agent for external application was coated on the local portion of one group to which bleomycin was administered subcutaneously, whereas the DNA-free preparation in Example 6 as a control was coated on the local portion of the other group to which bleomycin was administered subcutaneously. This coating was conducted once a day every day over 5 weeks from the start-up of the bleomycin treatment. The day after the completion of the coating, the thickness of the skin was measured. The value (Double skin thickness ± SE (mm)) of the control group was 5.27±0.66, whereas that of the DNA-treated group was 4.13±0.39. That is, the significant inhibition of the sclerema was observed in the group treated with DNA-containing preparation.

We claim:

1. In a troche composition containing a physiologically active ingredient for modulating an immunofunction through oral administration, the improvement comprising said physiologically active ingredient comprising DNA having at least eight bases, including at least one CpG sequence, extracted from a cell of a procaryote.

2. The troche composition as claimed in claim 1, wherein the procaryote is selected from the group consisting of *Bacillus natto, Bacillus subtilis*, a lactic acid bacterium, an amino acid-producing bacterium and *Escherichia coli*.

3. The troche composition as claimed in claim 1, wherein the DNA's molecular weight is lowered through sonication or restriction endonuclease treatment.

4. The troche composition as claimed in claim 1, additionally comprising a foodstuff.

5. The troche composition as claimed in claim 1, additionally comprising a feed.

6. The troche composition as claimed in claim 1, wherein the DNA is in the form of a sodium salt.

7. A method of inhibiting the growth of a tumor by orally administering an immunomodulating composition containing a physiologically active ingredient in which the improvement comprises said physiologically active ingredient comprising DNA having at least eight bases, including one CpG sequence, extracted from a cell of a procaryote.

* * * * *